US009028558B2

(12) United States Patent
Halldorsson et al.

(10) Patent No.: US 9,028,558 B2
(45) Date of Patent: May 12, 2015

(54) SUSPENSION LINER HAVING MULTIPLE COMPONENT SYSTEM

(71) Applicant: Ossur HF, Reykjavik (IS)

(72) Inventors: Olafur Freyr Halldorsson, Mosfellsbaer (IS); Maitland Craig Mackenzie, Orlando, FL (US)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 13/893,977

(22) Filed: May 14, 2013

(65) Prior Publication Data

US 2013/0331952 A1   Dec. 12, 2013

Related U.S. Application Data

(63) Continuation-in-part of application No. 12/947,944, filed on Nov. 17, 2010, now Pat. No. 8,828,094.

(60) Provisional application No. 61/261,863, filed on Nov. 17, 2009.

(51) Int. Cl.
*A61F 2/78* (2006.01)
*A61F 2/80* (2006.01)
*A61F 2/50* (2006.01)

(52) U.S. Cl.
CPC ........ *A61F 2/7812* (2013.01); *A61F 2002/7818* (2013.01); *A61F 2002/7837* (2013.01); *A61F 2/80* (2013.01); *A61F 2002/5056* (2013.01); *A61F 2002/785* (2013.01); *A61F 2240/001* (2013.01); *A61F 2250/0014* (2013.01); *A61F 2250/0018* (2013.01)

(58) Field of Classification Search
CPC .......... A61F 2/7812; A61F 2002/7818; A61F 2002/7837
See application file for complete search history.

(56) References Cited

U.S. PATENT DOCUMENTS

| 3,587,572 A | 6/1971 | Evans |
| 4,908,037 A | 3/1990 | Ross |
| 4,923,474 A | 5/1990 | Klasson et al. |
| 5,263,923 A | 11/1993 | Fujimoto |
| 5,308,305 A | 5/1994 | Romney |
| 5,376,129 A | 12/1994 | Faulkner et al. |

(Continued)

FOREIGN PATENT DOCUMENTS

| CN | 1427701 A | 7/2003 |
| CN | 201088641 Y | 7/2008 |

(Continued)

OTHER PUBLICATIONS

International Search Report corresponding to PCT/2010/002990 dated Feb. 21, 2011.

(Continued)

*Primary Examiner* — David H Willse
(74) *Attorney, Agent, or Firm* — Workman Nydegger

(57) ABSTRACT

A suspension liner for a residual limb has a liner body with a plurality of anterior and posterior projections formed from a thickness of the liner body. Medial and lateral tendons are located between and correspond to profiles of the plurality of the anterior and posterior projections such that the medial and lateral tendons are located on opposed sides of the liner body relative to one another. The medial and lateral tendons flare circumferentially toward proximal and distal sections of the liner body.

19 Claims, 6 Drawing Sheets

(56) References Cited

U.S. PATENT DOCUMENTS

| | | | |
|---|---|---|---|
| 5,507,834 A | 4/1996 | Laghi | |
| 5,718,925 A | 2/1998 | Kristinsson et al. | |
| 5,728,167 A | 3/1998 | Lohmann | |
| 5,830,237 A | 11/1998 | Kania | |
| 5,888,216 A | 3/1999 | Haberman | |
| 5,971,729 A | 10/1999 | Kristinsson et al. | |
| 5,972,036 A | 10/1999 | Kristinsson et al. | |
| 6,110,134 A | 8/2000 | Clark, Jr. et al. | |
| 6,136,039 A | 10/2000 | Kristinsson et al. | |
| 6,231,617 B1 | 5/2001 | Fay | |
| 6,416,703 B1 | 7/2002 | Kristinsson et al. | |
| 6,485,776 B2 | 11/2002 | Janusson et al. | |
| 6,706,364 B2 | 3/2004 | Janusson et al. | |
| 6,918,936 B2 | 7/2005 | Hellberg | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,169,189 B2 | 1/2007 | Bjarnason et al. | |
| 7,909,884 B2 | 3/2011 | Egilsson et al. | |
| 8,034,120 B2 | 10/2011 | Egilsson et al. | |
| 8,052,760 B2 | 11/2011 | Egilsson et al. | |
| 8,382,852 B2 | 2/2013 | Laghi | |
| 8,828,094 B2 | 9/2014 | Halldorsson | |
| 2005/0101693 A1 | 5/2005 | Arbogast et al. | |
| 2005/0149202 A1 | 7/2005 | Schaffer et al. | |
| 2006/0106328 A1 | 5/2006 | Sieller et al. | |
| 2006/0111792 A1 | 5/2006 | Shannon | |
| 2007/0061017 A1 | 3/2007 | Wilson | |
| 2007/0162153 A1 | 7/2007 | Barnes et al. | |
| 2009/0036999 A1 | 2/2009 | Egilsson et al. | |
| 2009/0132056 A1 | 5/2009 | Kania | |
| 2010/0016993 A1 | 1/2010 | Mackenzie | |
| 2011/0118854 A1 | 5/2011 | Halldorsson | |
| 2013/0085435 A1 | 4/2013 | Murphy et al. | |

FOREIGN PATENT DOCUMENTS

| | | | |
|---|---|---|---|
| DE | 2127269 | 12/1972 | |
| DE | 100 40 955 A1 * | 3/2002 | ............ A61F 2/78 |
| SU | 1739990 | 6/1992 | |
| WO | 97/17917 | 5/1997 | |
| WO | 2011/062619 A1 | 5/2011 | |

OTHER PUBLICATIONS

Writen Opinion of the International Searching Authority correspondign to PCT/2010/002990 dated Feb. 21, 2011.

International Search Report and Written Opinion of the International Searching Authority from Corresponding International Application No. PCT/US2014/037991, mailed Sep. 23, 2014.

International Search Report and the Written Opinion of the International Searching Authority from International Application No. PCT/US2014/055070, Nov. 21, 2014.

* cited by examiner

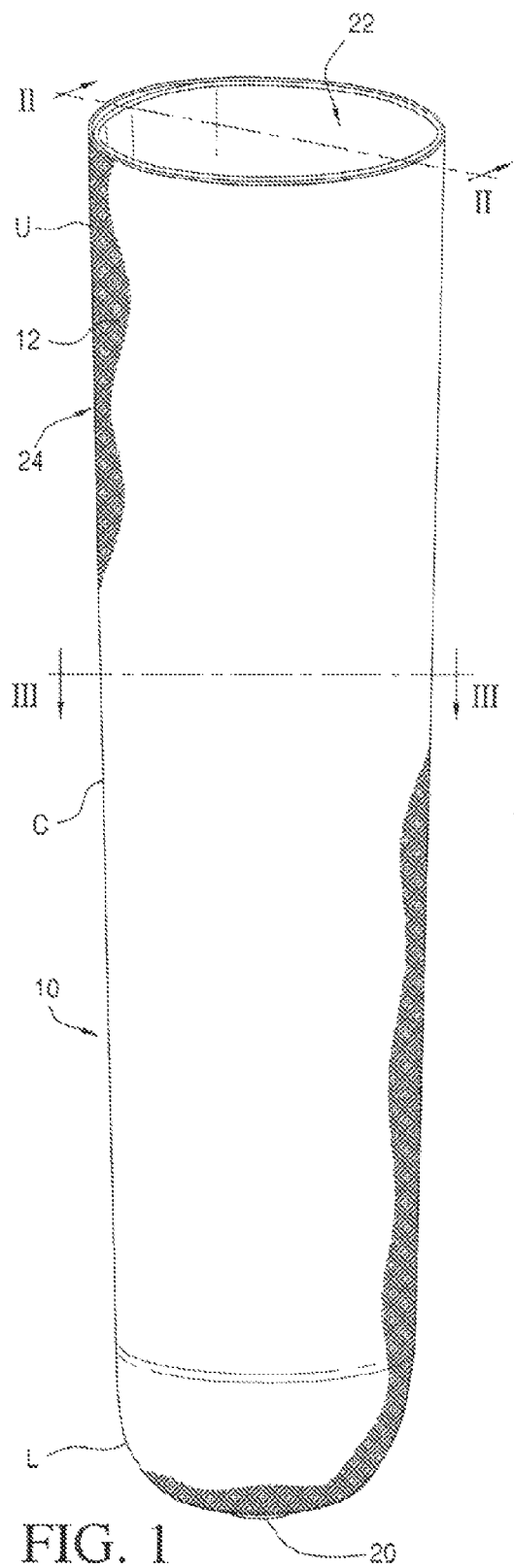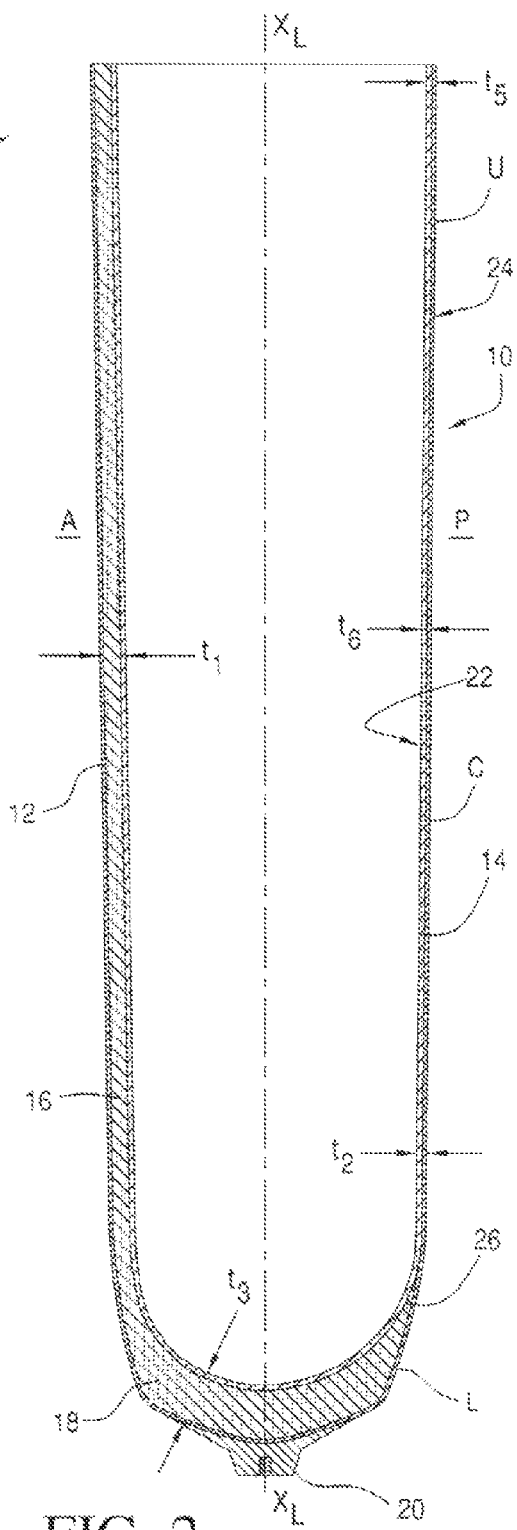
FIG. 1
FIG. 2

SUSPENSION LINER HAVING MULTIPLE COMPONENT SYSTEM

TECHNICAL FIELD

The present application is directed to a liner or sleeve having a multiple component system, and more specifically to suspension liners formed from a plurality of different layers having different material properties and thicknesses.

BACKGROUND

Prosthetic suspension liners or sleeves have been described in prior patents, such as U.S. Pat. No. 4,923,474, issued May 8, 1990; U.S. Pat. No. 6,136,039, issued Oct. 24, 2000; U.S. Pat. No. 6,485,776, issued Nov. 26, 2002; U.S. Pat. No. 7,118,602, issued Oct. 10, 2006; and U.S. Pat. No. 7,169,189, issued on Jan. 30, 2007, each of which are incorporated herein by reference. These liners or sleeves may be fabricated of elastic or elasticized materials, and are used to cushion a post-operative stump or residual limb with respect to a prosthesis, such as a socket, that is installed over the residual limb and coupled to the liner or sleeve by a conventional locking element.

It is highly desirable that these liners conform closely to the residual limb, accommodate all surface contours and sub-surface bone elements of the residual limb, and provide a comfortable cushion between the residual limb and the hard socket of the prosthesis that is to be fitted over the residual limb.

Special silicone rubber or elastomeric materials have been formulated as suitable substances for suspension liners. Such elastomeric materials having an appropriate hardness (or softness), elongation, tensile, and other properties, such as bio-inertness (resulting in no skin reaction), have been successfully used for suspension liners.

Much like liners, orthopedic or prosthetic sleeves are provided for supporting and reinforcing muscles, joints, and extremities of those in need of assistance, and moreover provide an airtight seal between a residual limb of an amputee and a prosthesis socket worn by the amputee. Moreover, such sleeves are not limited to use for amputees but may be applied to existing limbs to provide support in a manner associated with conventional orthopedic devices. Orthopedic and prosthetic sleeves of this type are described in U.S. Pat. No. 6,592,539 issued Jul. 15, 2003.

These sleeves may be similarly fabricated of elastic or elasticized materials as in liners. Typically, these sleeves are formed by joining sections of elasticized fabric shaped in tubular form and joined at their axial ends to form a tubular sleeve extending in an axial direction. The sleeves may be cylindrical, curved or possess other anatomically conforming shapes.

While effective solutions have been proposed and implemented, it is still highly desirable to improve comfort of such liners or sleeves to increase their ability to conform to irregularities on a residual limb, to accommodate a wider variety of limbs with fewer sizes of liners, and provide an amputee with enhanced comfort at a residual limb interface with a prosthesis while maintaining sufficient strength and durability. Moreover, it is particularly desirable to provide a liner or sleeve wherein means is made available to distribute pressure of the liner against a prosthesis while providing superior stretching over known liners and sleeves.

For the foregoing reasons, there is a need to provide improved liners and sleeves that impart improved conformance, pressure distribution, comfort and stretching while maintaining sufficient durability and strength for their requisite applications.

SUMMARY

In accordance with the illustrated embodiments of the invention, a residual limb suspension liner satisfies the aforementioned needs. The illustrated embodiment displays the liner as being particularly tailored for a prosthesis. The liner forms a closed-ended, tubular sleeve having a longitudinal axis, and defines along the axis a lower portion, an upper portion, and a center portion extending between the lower and upper portions. The liner is also divided along an anterior-posterior plane between anterior and posterior aspects or sides of the liner.

The liner includes a first layer defined by a first elastomeric material and has first and second surfaces spaced by a first thickness. The first surface forms a continuous circumferential internal surface of the liner.

The liner also has a second layer defined by a second elastomeric material and defines first and second surfaces spaced by a second thickness. The second layer first surface is adjacent and integrally joined to the first layer second surface. The second layer has a variable radial thickness over the anterior aspect of the liner. Both the second layer and portions of the first layer may be covered continuously by a fabric layer.

The first layer is preferably stiffer than the second layer, whereas the in the first elastomeric material has a greater stiffness than the second elastomeric material. The second layer provides cushioning for at least the anterior of the liner, particularly for the tibia of a trans-tibial amputee. The second layer serves as a soft pad over bony areas of a residual limb, to improve skin condition or mitigate issues due to a breakdown of the skin at such areas.

The first layer may continuously extend about anterior and posterior aspects of the internal surface of the liner. The second layer is preferably located only along a posterior aspect of the liner in the lower portion of the liner. The second layer may extend about the entirety of the lower portion of the liner, as well as from the upper and center portions of the liner along the anterior aspect of the liner, and terminate at the lower portion at the posterior aspect.

The thickness of the first layer may be consistently the same about the circumference of the liner. The thickness of the second layer may also vary as extending to first or lateral and second or medial sides of the liner. The thickness of the first layer adjacent the second layer may remain consistently the same. According to a variation of the liner, the second layer may extend less than 50% over the total surface area of the first surface of the first layer.

According to an embodiment of the liner, the second layer second surface forms a plurality of peripheral profiles extending radially outwardly relative to the longitudinal axis. The first layer second surface and the second layer first surface are continuously devoid of the peripheral profiles. The second layer may form an undulating wall thickness along an elongated portion thereof, and the undulating wall thickness may be formed only along the second layer second surface.

The peripheral profile allows for easier knee flexion at the knee with improved cushioning, while the stiffer first layer allows for stability and increased proprioception of the liner, particularly in areas outside of the second layer. The second layer also provides cushioning at the lower or distal end of the liner by increasing the use of softer elastomeric material and a greater thickness of such material.

The increased stability is due in part to a thinner use of the first, stiffer elastomeric material at the posterior aspect of the liner, thereby allowing the residual limb to be in closer contact with a socket worn with the liner to form part of the prosthesis. The increase in stability also attributes to improved control for the amputee.

In another embodiment, a suspension liner includes a liner body having proximal and distal sections with a central section located therebetween. The liner has a plurality of anterior and posterior projections formed from a thickness of the liner body. A tendon is located between and corresponding to a profile of the plurality of the anterior and posterior projections. The tendon circumferentially separates the plurality of anterior and posterior projections.

The plurality of the anterior projections may taper in length toward the proximal and distal sections of the liner, and the tendon flares circumferentially according to the taper of the plurality of anterior projections. The plurality of anterior projections is spaced by grooves formed into the thickness of the liner body and may be delimited by a contour of proximal and distal sections of the liner body adjacent the plurality of anterior projections such that the plurality of anterior projections extends short of or to the contour.

The plurality of anterior projections may increase or decrease in height relative to their location along the liner body. Grooves formed into the thickness of the liner body and separating the projections may vary in height relative to the size of the adjacent projections.

The plurality of anterior projections may be delimited by a contour of proximal and distal sections adjacent the plurality of anterior projections such that the plurality of anterior projections extend short of or to the contour. The plurality of anterior projections may have a greatest circumferential length at the central section of the plurality of anterior projections. The plurality of anterior projections may have proximal projections located at a proximal section of the plurality of anterior projections having a shorter height than the central projections located at the central section. The plurality of anterior projections may have distal projections located at a distal section having a height shorter than the central projections and taller than the proximal projections.

The tendon is located on a medial side of the liner body, and a lateral tendon is located on a lateral side of the liner body. The medial and lateral tendons separate the plurality of anterior and posterior projections. The tendon may have a narrowest width corresponding to a central section of the plurality of anterior and posterior projections, and the tendon may have a variable width between proximal and distal sections of the plurality of anterior and posterior projections. The tendon may be thicker about a circumference of the liner corresponding to the plurality of the anterior and posterior projections such that the tendon has a greater thickness than any of the plurality of projections.

BRIEF DESCRIPTION OF THE DRAWINGS

The numerous other advantages, features and functions of embodiments of a suspension liner will become readily apparent and better understood in view of the following description and accompanying drawings. The following description is not intended to limit the scope of the suspension liner, but instead merely provides exemplary embodiments for ease of understanding.

FIG. 1 is an elevational view of an embodiment of a suspension liner as a locking liner including features of the present invention.

FIG. 2 is a cross-sectional view taken along line II-II of FIG. 1.

Figure 3:
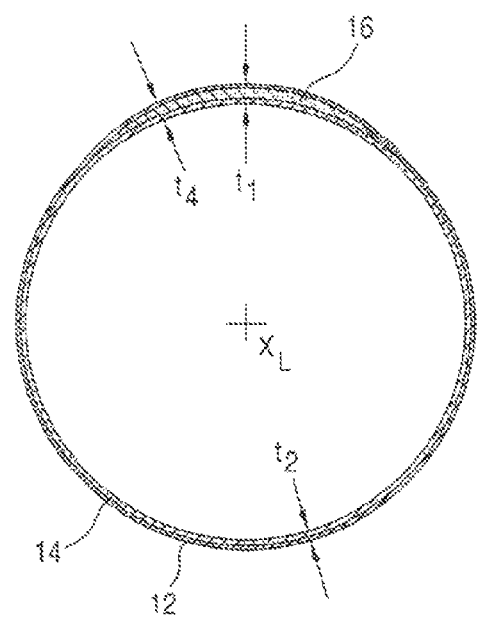
FIG. 3 is a cross-sectional view taken along line III-III of FIG. 1.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a liner, and in no way limit the structures or configurations of a liner thereof according to the present disclosure.

DETAILED DESCRIPTION OF VARIOUS EMBODIMENTS

A better understanding of different embodiments of the invention may be had from the following description read in conjunction with the accompanying drawings in which like reference characters refer to like elements.

FIGS. 1-4 illustrate an embodiment of a prosthetic suspension liner 10 having a multiple component system. The liner 10 defines a close-ended tubular sleeve having a longitudinal axis $X_L$-$X_L$, and is configured to envelop a distal area of a residual limb (not shown). The liner 10 defines an upper or proximal portion U, a lower or distal portion L, and a center portion C axially extending between the upper and lower portions U, L. The liner is also divided along an anterior-posterior A-P plane between anterior and posterior sides or aspects A, P of the liner.

Figure 4:
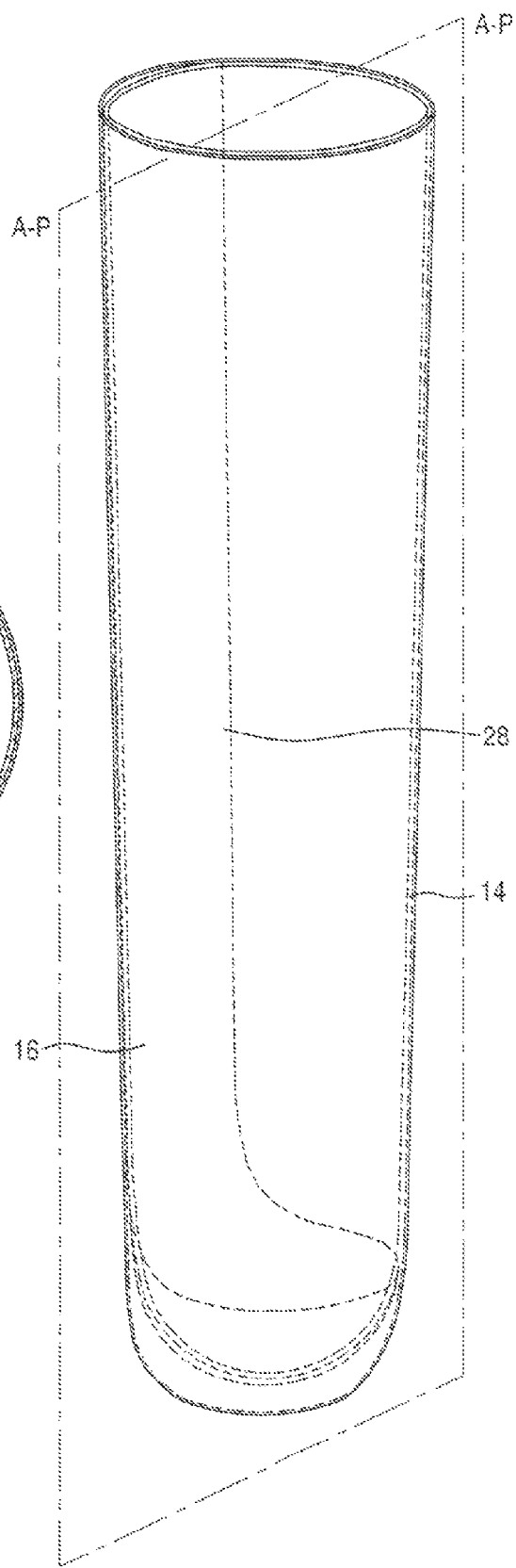
FIG. 4 is a perspective view showing the liner according to FIG. 1 as a cushion liner.
Figure 5:
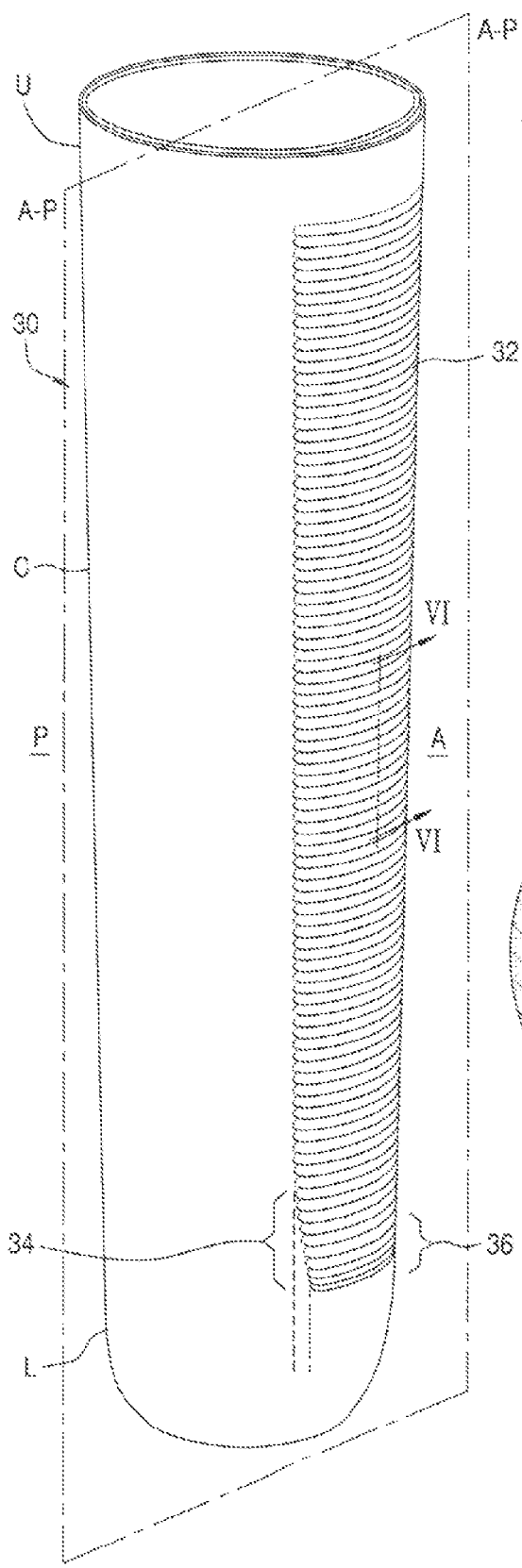
FIG. 5 is an elevational view of another embodiment of a suspension liner as a cushion liner.

An elasticized fabric or textile layer 12 continuously covers the outer surface 24 of the liner 10 without interruption. The liner is intended to be air-tight when donned over a residual limb. As illustrated in FIGS. 1 and 2, the liner may include a prosthesis connecting element 20, as would be understood by the skilled person in the field of prosthetic devices, when the liner is modified as a locking liner. FIGS. 4 and 5 depict the liner as a cushion liner without a connecting element.

The liner 10 includes a first component or layer 14 defined by a first elastomeric material. The first layer defines first and second opposed surfaces, such that the first layer 14 has a first surface which forms a circumferential internal surface 22 to the liner. The inner surface may be substantially smooth and continuous without interruption so as to facilitate donning of the liner on a residual limb. The liner 10 also includes a second component or layer 16 defined by a second elastomeric material. The first and second layers 14, 16 are contiguous and integrally joined to each other along only a portion of the second surface of the first layer 14. The interface between the layers 14, 16 is seamless and integrally permanent.

In observing the embodiments of FIGS. 3 and 4, the second layer 16 does not circumferentially extend about the liner 10, but instead the thickness is radially variable across the anterior aspect of the liner. In short, the second layer 16 is only provided in a localized region of the liner. According to this embodiment, the second layer 16 particularly corresponds to the tibial portion of the liner and extends along the anterior aspect A of the liner thereby providing additional comfort to the wearer along this region.

In this embodiment, the first layer 14 is stiffer than the second layer 16, and the first elastomeric material has a greater hardness than the second material. In other variations, the first and second layers may define different relationships regarding their respective hardness.

The combination of the first and second layers 14, 16 define different thicknesses at various regions of the liner, and these layers themselves may have different thicknesses over the liner.

In reference to FIGS. 2 and 3, the liner 10 defines a greater thickness at the tibial portion of the liner as represented by a side of the liner including the second layer 16 in combination with the first layer 14. Particularly, the anterior aspect A of the liner defines a thickness $t_1$ including both the first and second layers 14, 16 in combination with the fabric layer 12. The thickness $t_2$ at the posterior aspect P at or about the same height as the thickness $t_1$ is smaller than the thickness $t_1$.

The thickness $t_2$ includes only the first layer 14 in combination with the fabric layer 12, with the first layer 14 having a generally consistent circumferential thickness $t_6$ over at least the central portion C across both the anterior and posterior aspects A, P of the liner. It will be understood that the first layer 14 preferably has thickness $t_6$ extending over the second layer 16 in the lower portion L liner.

The lower portion L of the liner includes a cushioned region 18 having both the first and second layers 14, 16 wherein the second layer 16 has a greater thickness than at other portions, as evidenced by thicknesses $t_3$. As the second layer 16 terminates at the lower portion on the posterior aspect P of the liner, the thickness of the second layer gradually tapers so that the second layer 16 no longer exists and only the first layer 14 continues along the posterior aspect P of the liner. In particular, the thickness of the second layer 16 tapers as it extends from the anterior aspect A to the posterior aspect P across the lower portion L of the liner.

In particular reference to FIG. 3, the thickness $t_4$ of the second layer 16 on the anterior aspect A of the liner in the central and upper portions C, U is a radially variable, in that the thickness tapers toward the first or lateral, and second or medial sides of the liner. The second layer 16 may be formed along the entirety of the anterior aspect of the liner, or, as shown in FIG. 4, only along a strip of the anterior aspect of the liner and less than the entirety of the anterior aspect of the liner.

In order to illustrate the thickness differences in an exemplary embodiment of the suspension liner, the thickness $t_1$ formed by the combination of the textile layer and the first and second layers on the anterior aspect A of the liner may be 5.5-7.5 mm, the thickness $t_2$ may be 1.5-3.5 mm for the combination of the first layer and the textile layer, and the thickness at $t_3$ formed by the combination of the textile layer and first and second layers at the lower portion may be 10.0-14.0 mm and increase to a maximum at the longitudinal axis, tapering differently in thickness on both sides thereof.

The liner embodiment may be configured so that the second layer is particularly positioned at locations of the liner either including or excluding the anterior aspect A. According to one variation, the second layer defines a front outer portion of the liner and the first layer defines at least the rear outer portion of the liner. In this variation, the second layer extends over less than 50% of the total surface area of the second surface of the first layer. Of course, other ratios are available as long as the second layer extends less than the total surface area of the first surface of the first layer.

It should be noted that the liner is not limited to having the second layer only defined along the anterior aspect of the liner, and it is envisioned that the second layer may extend in part into the upper and center portions of the posterior aspect of the liner.

It will be noted that the liner may have a circumferential taper as the liner approaches a posterior end of the liner, as denoted by thickness $t_5$.

According to a variation in FIG. 4, the second layer circumferentially extends about a lower, closed-ended portion of the liner and, a spline 28 divides the first and second layers to provide a clear demarcation between the first and second layers preferably along the anterior aspect of the liner.

Turning to another embodiment of the liner, the second layer forms an undulating wall thickness along an elongated portion thereof. In a variation, the undulating wall thickness is formed only along the second layer, such that the first layer second surface and the second layer first surface are continuously devoid of the peripheral profiles. In another variation, the undulating wall thickness may be formed by both the first and second layers.

The undulating wall thickness may be formed only in the second layer and the second layer. For example, in a liner designated for a trans-tibial amputee, the undulating wall thickness corresponds to the anterior aspect of the residual limb so as to facilitate the bending of the liner.

Figure 6:
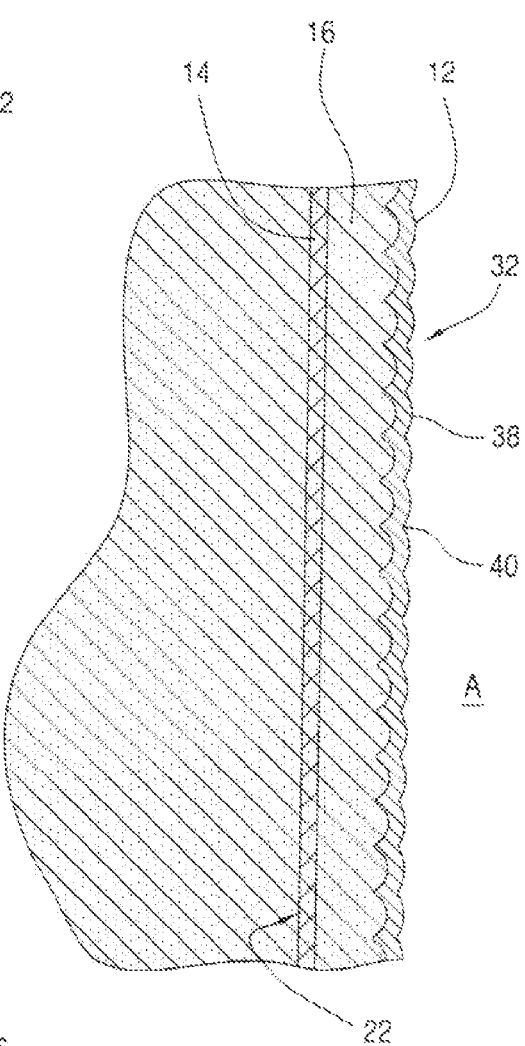
FIG. 6 is cross-sectional view of a cross-section view taken along line VI-VI of FIG. 5.

According to the embodiment depicted by FIGS. 5 and 6, a liner 30 defines a plurality of peripheral profiles 32 extending generally between the proximal and distal ends of the liner 30 generally along the anterior aspect A of the liner. According to this embodiment, the peripheral profiles are located only another anterior aspect of the liner such that the proximal and distal ends and at least the posterior aspect P of the liner are devoid of the peripheral profiles.

As shown in FIGS. 5 and 6, the peripheral profiles 32 are defined as a plurality of adjacent projections that extend annularly about the axis of the liner 30. The projections 38 have a generally uniform, rounded outline, and are axially spaced at troughs 40 from one another. The projections 32 generally distend radially outwardly from the liner 30, and the internal surface 22 of the liner 30 is substantially smooth.

According to this embodiment, the peripheral profiles 32 are formed only in the second layer 16, whereas the first layer 14 lacks the peripheral profiles. The elasticized fabric 12 generally follows the contours of the peripheral profiles 32.

FIG. 5 shows a variation of a liner having the peripheral profiles in that a plurality of profiles 34 taper in width as they draw closer to the distal end of the liner. In addition, FIG. 5 shows a plurality of profiles 36 having a taper in height as they draw closer to the distal end of the liner. In other variations, the peripheral profiles may have varying thicknesses and different spacing along the liner. The liners according to the invention may either omit or have any combination of these peripheral profiles described herein and described in U.S. Pat. No. 7,118,602, incorporated herein by reference.

While in each of the liner embodiments described above the distal portion is generally without peripheral profiles, liner embodiments of the invention may be configured so that at least a section of the distal portion may be provided with peripheral profiles such as those discussed above. It will be noted that embodiments of the liner may have variable wall thicknesses at least in regions of the peripheral profiles. Such variable wall thickness improves the ability to stretch the liner and additionally provides cushioning by more aptly distributing pressure against a prosthesis such as a hard socket.

Moreover, the peripheral profile portions of the liners may be combined or modified as considered expedient by one of ordinary skill in the art to improve stretchability and comfort for an amputee.

In each of the embodiments shown herein, the liner is intended for use between a residual limb and a prosthesis, such as a hard socket, and to be air-tight when donned over a residual stump. The internal surface of the liner may be formed of a layer of silicone elastomer, therefore serving as a skin interface. Silicone is advantageous in that it allows for different levels and softness and strength to be incorporated into the liners of the present application. Moreover, silicone permits the addition of selected supplements, such as petroleum jelly and aloe vera, which improve skin care and comfort.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of the liner when a prosthesis is worn thereover.

It is envisioned that any of the aforementioned liners, and subsequently discussed sleeves, may be constructed having a soft internal silicone elastomer layer and a relatively harder external silicone elastomer layer in accordance with U.S. Pat. No. 6,136,039, incorporated herein by reference.

A prosthesis connecting element, as shown in FIG. 2, may be provided at the distal end of any of the embodiments of the inventive liner of the present application. The connecting element may be embedded in a silicone elastomer layer or layers of the liner, or may be intimately bonded to the distal end of the liner. An example of a connecting element is discussed in U.S. Pat. No. 6,136,039. Alternatively, the liner may be provided without a connecting element, and have a distal end portion with enhanced cushioning as in what is commonly known as a "Cushion" type liner.

A liner in accordance with this disclosure may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, incorporated herein by reference. In addition, any of the liners and sleeves mentioned herein may be constructed in the manner prescribed by U.S. Pat. No. 4,923, 474.

Any of the liner embodiments described herein may include a sealing arrangement, as taught in any one of U.S. Pat. Nos. 7,025,793 and 7,749,281, and U.S. patent application publication 2007/0123998, each of which is incorporated herein by reference.

The embodiments of the inventive liner of the present application may be constructed according to the molding methods described in U.S. Pat. No. 6,485,776, the entirety of which is incorporated herein by reference. In making the liners having peripheral profiles, the profiles may be imparted to the liner by appropriate molding techniques, such as female molds which have the impression of the desired peripheral profiles of the invention.

Figure 7:
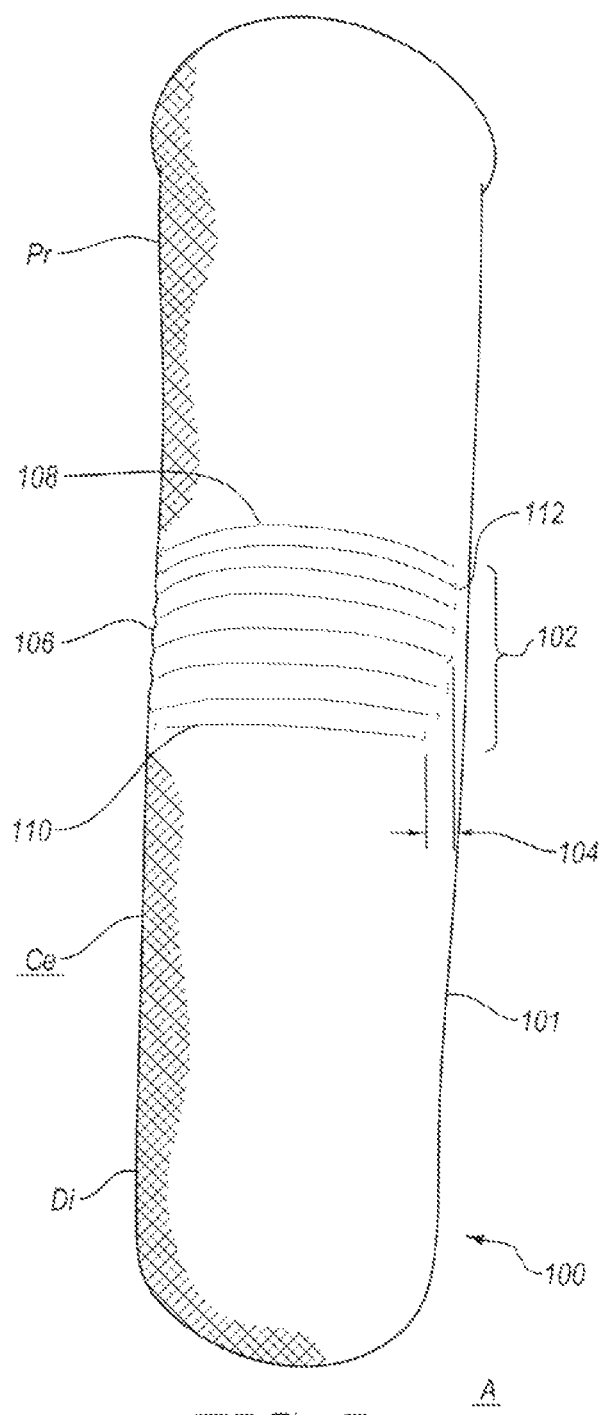
FIG. 7 is an elevational frontal view of another embodiment of a suspension liner.
Figure 8:
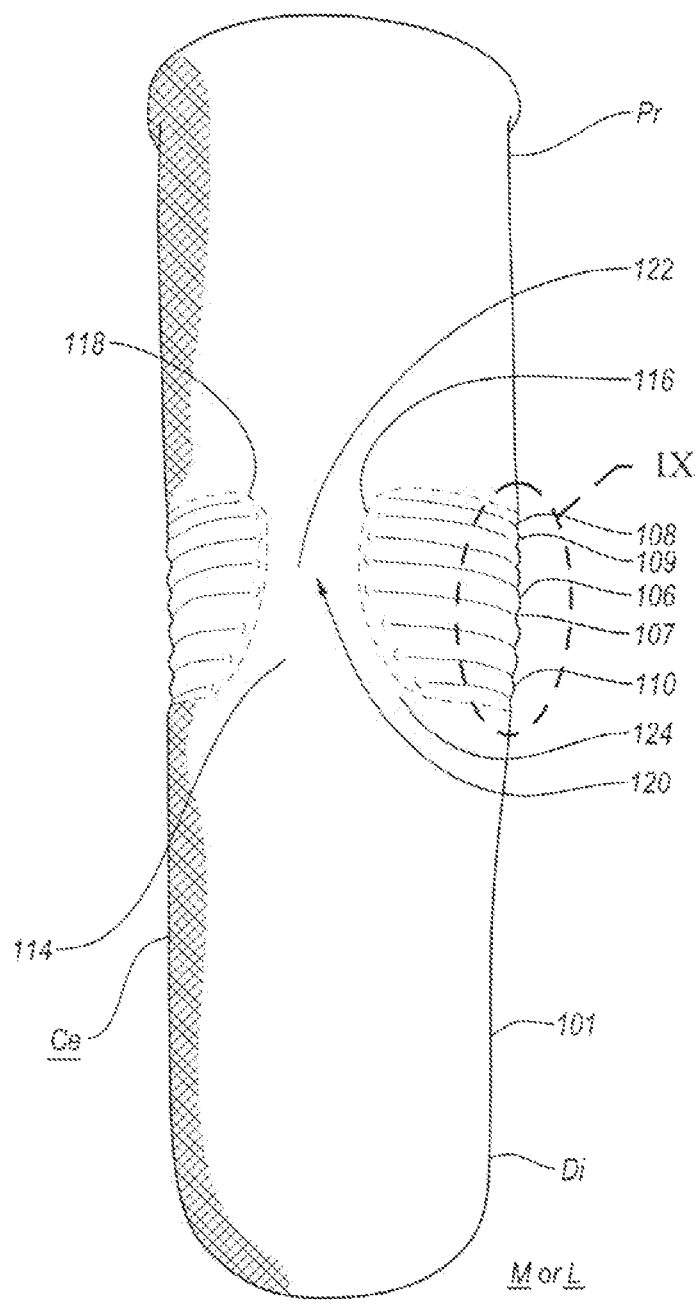
FIG. 8 is an elevational side view of the embodiment of FIG. 7.
Figure 9:
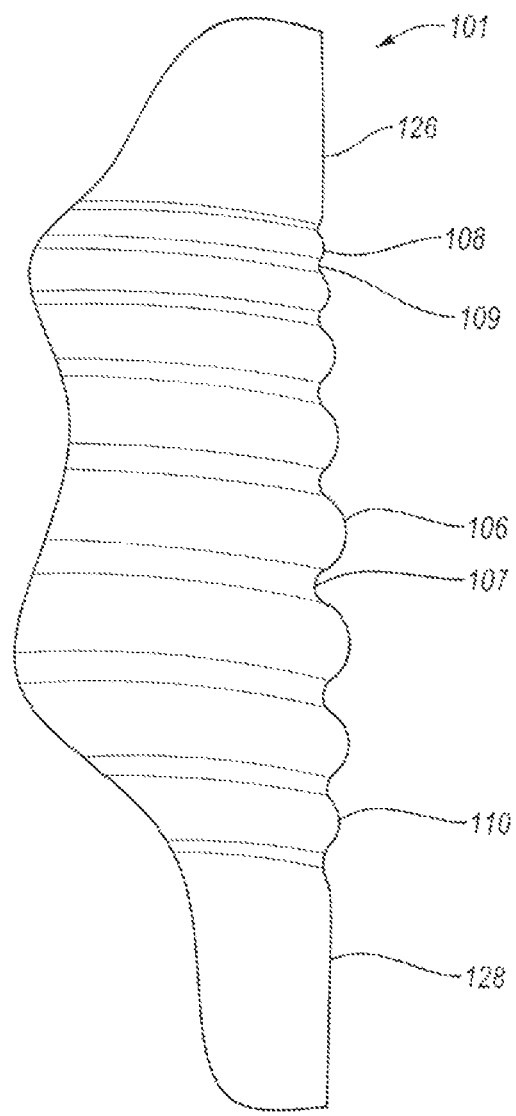
FIG. 9 is a detail view of section IX taken from FIG. 8.

In FIGS. 7-9, a suspension liner 100 defines a liner body 101 and a plurality of projections 102 over a discrete region 112 of the liner body 101. According to this embodiment, the liner 100 is arranged for a transtibial residuum, wherein the discrete region 112 corresponds to the user's knee. The projections over the anterior side of the user's knee facilitate bending of the liner when the knee goes into flexion, particularly over the user's knee cap, whereas the projections along the posterior side of the user's knee prevent bunching of the liner over the popliteal region of the user's knee.

In FIG. 7 showing an anterior side A of the liner, the projections 102 have a taper 104, much as in the embodiment of FIG. 5. The plurality of projections 102 defines differently sized projections having different heights, wherein proximal projections 108 located toward the proximal portion Pr have a short height, the central or middle projections 106 at generally the center portion Ce have a greatest height, and the distal projections 110 located toward the distal portion Di have a height less than the central projections 106.

Unlike the other embodiments, the discrete region 112 is composed of anterior and posterior projections 116, 118 separated by a tendon 120 on both the medial and lateral sides of the liner 100. Thus, the anterior and posterior projections 116, 118 are separated from one another circumferentially by the tendon 120 which continuously blends with the surface of the liner body 101.

The tendon 120 may define a recessed region forming indicia, such a logo which is molded into the liner body yet preferably to a depth less than the depth of grooves located between the projections 102. The tendon 120 defines a central region 122 having a narrower width than end portions 124. The end portions 124 of the tendon 120 flare toward the anterior and posterior sides. The configuration of the narrow central region 122 facilitates bending of the knee, whereas the flaring proximal and distal end portions 124 provide enhanced stability and strength for the liner.

The boundaries of the anterior and posterior projections 116, 118 are sized accordingly to the flared portions which result in a gradual taper in length of the projections toward the proximal and distal sections of the liner.

The tendon 120 is arranged to provide enhanced stability along the medial and lateral sides, whereas the plurality of projections 102 along the anterior and posterior sides facilitate bending of the knee. The arrangement of the tendon eliminates the need for a reinforcement layer or laminated structure about the circumference of the liner corresponding the user's knee, as reinforcement is created by the thickness of the tendon and the same material forming the wave feature.

FIG. 9 depicts how both the projections and the grooves spacing the grooves may be differently sized in height. For example, the shorter projections 108 have a corresponding narrow groove 109, whereas the taller projections 106, have correspondingly taller grooves 107. The projections 110 likewise may have correspondingly sized grooves. The shorter projections at the proximal end of the plurality of projections are arranged since less bending is required to provide more stability above the knee. The taller projections are arranged to maximize bending over the knee, whereas the distal or lower projections 110 are arranged to taper off the bending of the liner over the knee.

The projections may fall generally within a contour defined by bordering proximal and distal sections 126, 128 of the liner, meaning that the projections do not extend generally beyond the contour. From this arrangement the grooves extend deeper into the thickness of the liner body as the projections approach the center portion of the plurality of projections. From this configuration, the bendability at the anterior and posterior sides of the liner is at its greatest at the center portion of the plurality of projections and stiffness increases across the projections as they approach the proximal and distal sections 126, 128 of the liner.

The absence of projections over the tendon prevent bunching along the medial and lateral sides of the knee when the knee is in flexion, and withstands medial and lateral forces, thereby providing greater stability to the knee. The thickness of the liner may be increased over the tendon, by not just the absence of projections but by increasing the thickness relative to the proximal and distal sections of the liner, or there may be a taper of thickness from the tendon into the proximal and distal sections.

The liner 100 of FIGS. 7-9 may be a custom fitted liner corresponding to a particular geometry of an individual residuum. According to a method, a female mold is created corresponding to the user's residuum. A section of the female mold is arranged with a recess to accommodate a collar bearing a standard configuration of a "wave" feature or the aforementioned plurality of projections in reference to FIGS. 7-9.

The collar is placed on the mold in a recess formed on the female mold, and inspected for fit and appropriate placement to correspond to the user's knee. While the collar has a standard wave configuration, such as that defined in reference to FIGS. 7-9, multiple collars may be available according to ranges of sizes, lengths and differently sized and configured projections of the definitive liner and corresponding to an individual residuum.

A thin stocking is pulled over the collar for a vacuum wick. A film such as a thin layer of plastic may be pulled over the female mold for protection. A thicker film such as a thick layer of plastic is pulled over the female mold in order to produce an outer shell. The thicker film is heated to define the shape of the mold along with the profile of the collar and forms an outer shell. After cooling, the outer shell takes on a negative shape of the wave collar, and the mold.

The mold is trimmed so as to form a male mold, thereby reducing the size relative to the outer shell. A thin plastic is then pulled over the male mold, and the outer shell is placed over the male mold. A polymeric material, such as silicone, is injected between the outer shell and the male mold so as to form the liner having the plurality of projections corresponding to the wave collar, and the shape of the residuum based on the female mold.

The liner may be formed from a single layer and type of polymeric material such that the thickness defined between a substantially smooth inner surface of the liner and the outer surface of the liner body is formed by a single layer. Alternatively, the thickness may comprise multiple layers.

Of course, it should be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct suspension liner in accordance with principles of the present invention.

Although this invention has been disclosed in the context of certain exemplary embodiments and variations thereof, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A suspension liner for a residual limb, comprising:
a liner body having proximal and distal sections with a central section located therebetween, the liner body having an open end at a proximal end of the proximal section and a closed end at a distal end of the distal section;
a plurality of anterior projections formed from a thickness of the liner body;
a plurality of posterior projections formed from a thickness of the liner body;
a tendon located between and corresponding to a profile of the plurality of the anterior and posterior projections, the tendon having a central region defining a narrower width than anterior and posterior end portions, wherein the plurality of the anterior projections taper in length toward the proximal and distal sections of the liner, the tendon flares circumferentially according to the taper of the plurality of anterior projections.

2. The suspension liner of claim 1, wherein the tendon circumferentially separates the plurality of anterior and posterior projections.

3. The suspension liner of claim 1, wherein the plurality of anterior projections is spaced by grooves formed into the thickness of the liner body.

4. The suspension liner of claim 3, wherein the plurality of anterior projections is delimited by a contour of proximal and distal sections of the liner body adjacent the plurality of anterior projections such that the plurality of anterior projections extends short of or to the contour.

5. The suspension liner of claim 1, wherein the plurality of anterior projections increase in height toward a central section of the plurality of anterior projections.

6. The suspension liner of claim 5, wherein the plurality of anterior projections are spaced by grooves formed into the thickness of the liner body, the grooves increasing in height from a proximal section of the plurality of anterior projections toward the central section of the plurality of anterior projections.

7. The suspension liner of claim 6, wherein the plurality of anterior projections is delimited by a contour of proximal and distal sections adjacent the plurality of anterior projections such that the plurality of anterior projections extend short of or to the contour.

8. The suspension liner of claim 5, wherein the plurality of anterior projections has a greatest circumferential length at the central section of the plurality of anterior projections.

9. The suspension liner of claim 5, wherein the plurality of anterior projections has proximal projections located at a proximal section of the plurality of anterior projections having a shorter height than the central projections located at the central section.

10. The suspension liner of claim 9, wherein the plurality of anterior projections has distal projections located at a distal section having a height shorter than the central projections and taller than the proximal projections.

11. The suspension liner of claim 1, wherein the tendon is located on a medial side of the liner body, and a lateral tendon is located on a lateral side of the liner body, the medial and lateral tendons separating the plurality of anterior and posterior projections.

12. The suspension liner of claim 1, wherein the tendon has a narrowest width corresponding to a central section of the plurality of anterior and posterior projections.

13. The suspension liner of claim 1, wherein the tendon has a variable width between proximal and distal sections of the plurality of anterior and posterior projections.

14. The suspension liner of claim 1, wherein the tendon is thicker about a circumference of the liner corresponding to the plurality of the anterior and posterior projections.

15. The suspension liner of claim 1, wherein the tendon has a greater thickness than any of the plurality of projections.

16. A suspension liner for a residual limb, comprising:
a liner body having proximal and distal sections with a central section located therebetween, the liner body having an open end at a proximal end of the proximal section and a closed end at a distal end of the distal section;
a plurality of anterior projections formed from a thickness of the liner body and having variable lengths about the circumference of the liner body;
a plurality of posterior projections formed from a thickness of the liner body;
medial and lateral tendons located between and corresponding to a profile of the plurality of the anterior and posterior projections, the medial and lateral tendons located on opposed sides of the liner body relative to one another, the medial and lateral tendons having a central region defining a narrower width than anterior and posterior end portions, wherein the plurality of the anterior projections taper in length toward the proximal and distal sections of the liner, the tendon flares circumferentially according to the taper of the plurality of anterior projections.

17. The suspension liner of claim 16, wherein the plurality of anterior projections has variable heights and a plurality of grooves having variable heights space the anterior projections.

18. The suspension liner of claim 17, wherein the heights of the plurality of grooves correspond to the heights of the plurality of anterior projections.

19. A suspension liner for a residual limb, comprising:
a liner body having proximal and distal sections with a central section located therebetween, the liner body having an open end at a proximal end of the proximal section and a closed end at a distal end of the distal section;
a plurality of anterior projections formed from a thickness of the liner body;
a plurality of posterior projections formed from a thickness of the liner body;
medial and lateral tendons located between and corresponding to a profile of the plurality of the anterior and posterior projections, the medial and lateral tendons located on opposed sides of the liner body relative to one another, the medial and lateral tendons flare outwardly circumferentially toward proximal and distal sections of the plurality of anterior and posterior projections, the medial and lateral tendons having a thickness formed from the liner body at least or greater than a thickness of the liner body across the plurality of anterior projections.

\* \* \* \* \*